United States Patent [19]

Panster et al.

[11] Patent Number: 5,219,899
[45] Date of Patent: Jun. 15, 1993

[54] PASTY DENTAL MATERIAL WHICH IS AN ORGANOPOLYSILANE FILLER COMBINED WITH A POLYMERIZABLE BONDING AGENT

[75] Inventors: Peter Panster, Rodenbach; Ralf Janda, Bad Homburg; Peter Kleinschmidt, Hanau, all of Fed. Rep. of Germany

[73] Assignee: Degussa Aktiengesellschaft, Frankfurt am Main, Fed. Rep. of Germany

[21] Appl. No.: 963,045

[22] Filed: Oct. 19, 1992

Related U.S. Application Data

[63] Continuation of Ser. No. 512,250, Apr. 20, 1990, abandoned.

[30] Foreign Application Priority Data

Apr. 22, 1989 [DE] Fed. Rep. of Germany ....... 3913252

[51] Int. Cl.$^5$ ........................................... C08F 283/12
[52] U.S. Cl. ................................. 523/118; 523/115; 523/116; 523/117; 525/479
[58] Field of Search ............... 525/479; 523/115, 116, 523/117, 118

[56] References Cited

U.S. PATENT DOCUMENTS

| | | | |
|---|---|---|---|
| 3,926,906 | 12/1975 | Lee et al. | 260/41 |
| 4,427,799 | 1/1984 | Orlowski et al. | 523/116 |
| 4,504,231 | 3/1985 | Koblitz et al. | 433/228 |
| 4,575,545 | 3/1986 | Nakos et al. | 526/242 |
| 4,690,986 | 9/1987 | Sasaki et al. | 525/479 |
| 4,717,599 | 1/1988 | Merrill | 525/479 |
| 4,728,709 | 3/1988 | Klemarczyk et al. | 528/15 |
| 4,826,893 | 5/1989 | Yamazaki et al. | 525/479 |
| 4,853,434 | 8/1989 | Block | 525/479 |
| 5,132,337 | 7/1992 | Panster et al. | 523/117 |

FOREIGN PATENT DOCUMENTS

| | | |
|---|---|---|
| 0381961 | 8/1990 | European Pat. Off. |
| 4002726 | 9/1990 | Fed. Rep. of Germany |
| 2051842 | 1/1981 | United Kingdom |

OTHER PUBLICATIONS

Chemical Abstract No. 53364 to Charles Mallon, vol. 100, 1984.

Primary Examiner—John C. Bleutge
Assistant Examiner—Margaret W. Glass
Attorney, Agent, or Firm—Beveridge, DeGrandi, Weilacher & Young

[57] ABSTRACT

A pasty dental material is disclosed which hardens to a high gloss polishable mass in the presence of an initiator. The mass is formed of a polymerizable bonding agent combined with an organosiloxane filler which contains units of the formula I

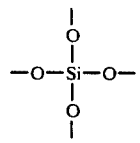

and which has been subjected to an after treatment which is a condensation in an autoclave for a period of time of 1 hour to 5 days at a temperature of 60° C. to 250° C. under a pressure which is the sum of the partial pressures at the given temperature.

12 Claims, No Drawings

PASTY DENTAL MATERIAL WHICH IS AN ORGANOPOLYSILANE FILLER COMBINED WITH A POLYMERIZABLE BONDING AGENT

CONTINUING APPLICATION DATA

This application is a continuation of U.S. patent application Ser. No. 07/512,250, now abandoned, filed Apr. 20, 1990, which application is entirely incorporated herein by reference.

INTRODUCTION AND BACKGROUND

The present invention concerns a pasty dental material, which hardens to a high-gloss polishable mass in the presence of an initiator, formed of a polymerizable bonding agent and a finely divided filler as the essential components. The material contains as a bonding agent at least one polymerizable methacrylate and an optionally silanizable, new filler based on functional polysiloxanes. It may also contain initiators to trigger polymerization, other fillers, such as finely ground glass types, highly dispersed silicas or previously produced polymers, pigments and stabilizers. Other additives such as softeners or impact strength improvers may also be contained in the composition.

The term "dental material" as used herein means, for example, filling materials for carious defects or other dental defects in the mouth, inlays, crown and bridge materials, veneers, sealing and protective coatings, plastic adhesives to fix inlays or crowns and bridges, stump build-up materials, denture materials as well as masses for the production of artificial teeth.

Standard dental masses of the above mentioned type contain at least one monomeric ester of methacrylic acid, but in most cases a mixture of several of such esters. Suitable monofunctional esters of methacrylic acid are e.g. methylmethacrylate, ethylmethacrylate, isopropylmethacrylate, n-hexylmethacrylate and 2-hydroxyethylmethacrylate.

Recently, multi-functional esters of methacrylic acid with a higher molecular weight have also been used frequently, such as ethylene glycol dimethacrylate, butandiol-1,4-dimethacrylate, triethylene glycol dimethacrylate, dodecandiol-1,12-dimethacrylate, decandiol-1,10-dimethacrylate, 2,2-bis-[p(γ-methacryloxy-β-hydroxypropoxy)-phenyl]-propane, the diaduct of hydroxyethylmethacrylate and trimethylhexamethylene diisocyanate, the diaduct of hydroxyethylmethacrylate and isophoron diisocyanate, trimethylolpropanetrimethacrylate, pentaerythritetrimethacrylate, pentaerythritetetramethacrylate and 2,2-bis[p(β-hydroxy-ethoxy)-phenyl]-propanedimethacrylate (bis-GMA).

The materials for dental use may, depending on the application purpose, be hardened in different ways. Dental filling materials exist in the form of photo-hardening as well as self-hardening (autopolymerizing) masses. The photohardening masses contain photoinitiators such as benzoinalkylether, benzilmonoketals, acylphosphinoxide or aliphatic and aromatic 1, 2-diketocompounds such as e.g. camphorquinone as well as polymerization accelerators such as aliphatic or aromatic tertiary amines (e.g. N,N-dimethyl-p-toluidine triethanolamine) or organic phosphites and harden when irradiated with UV or visible light.

The self-hardening materials consist as a rule of a catalyst paste and a base paste of which each contains a component of a redox system and which polymerize when the two components are mixed. One component of the redox system is in most cases a peroxide, such as e.g. dibenzoylperoxide, the other is in most cases a tertiary aromatic amine, such as e.g. N,N'-dimethyl-p-toluidine.

Other dental materials such as prosthesis plastics or plastic masses for the production of artificial teeth polymerize under heat application. The initiators in those cases are as a rule peroxides such as dibenzoylperoxide, dilaurylperoxide or bis(2,4-dichloro-benzoylperoxide).

Dental materials also contain as a rule pigments which—added in small amounts—act to match the color of the dental masses with the various shades of natural teeth. Suitable pigments are e.g. black iron oxide, red iron oxide, yellow iron oxide, brown iron oxide, cadmium yellow and orange, zinc oxide and titanium dioxide.

Dental materials further contain mostly organic or inorganic fillers in order to avoid a shrinking of the volume of the plastic mass during polymerization. Pure monomeric methylmethacrylate for instance shrinks during polymerization by about 20 vol %. By adding about 60 weight parts of solid methylmethacrylate-pearl polymer the shrinking may be reduced to about 5–6 vol % (see German Patent 24 03 211).

Other organic fillers are obtained by producing a polymer which consists essentially of esters of methacrylic acid and either is or is not cross-linked. This polymer optionally contains surface-treated fillers. If it has been produced as a polymer it may be added to the dental material in this form; if on the other hand it was produced by solventless polymerization in compact form it must be ground into a so-called splinter polymer before being added to the dental material.

Frequently used preformed polymers are in addition to the already mentioned filler-containing pearl and splinter polymers homopolymers of methyl methacrylate or, preferably non-cross-linked, copolymers of the methyl methacrylate with a low content of esters of the methacrylic acid or acrylic acid with 2 to 12 carbon atoms in the alcohol component, preferably in the form of a pearl polymer. Other suitable polymers are non-cross-linked products based on polyurethanes, polycarbonates, polyesters and polyethers.

Inorganic fillers are e.g. ground glasses or quartz with average particle sizes between 1 and 10 micrometers as well as highly dispersed silica with average particle sizes between 10 and 400 nm.

The glasses are preferably aluminumsilicate glasses which may be doped with barium, strontium or rare earths (see German Patent 24 58 380).

It should be noted in regard to the finely ground quartz or the finely ground glasses and the highly dispersed silica that the inorganic filler is as a rule silanized prior to the mixing with the monomers in order to achieve better bonding to the organic matrix. For this purpose the inorganic fillers are coated with silane coupling agents which in most cases have a polymerizable double bond for reaction with the monomeric esters of the methacrylic acid.

Suitable well known silane coupling agents for this purpose are e.g. vinyltrichlorosilane, tris-(2-methoxyethoxy)-vinylsilane, tris-(acetoxy)-vinylsilane and 3-methacryloyloxypropyltrimethoxysilane.

The initially mentioned, recently used monomers with higher molecular weight also result in a decrease of polymerization shrinkage. To these monomers the described inert inorganic finely ground glasses or organic fillers or mixtures thereof are added up to 85 wt %, which results in a further reduction of the shrinkage to ca. 1 vol %.

The inorganic fillers not only result in a decrease in polymerization shrinkage but in addition in a significant strengthening of the organic polymer structure.

This strengthening also shows itself in an improvement of mechanical characteristics and in an increase in wear resistance (R. Janda, Quintessenz 39, 1067, 1243, 1393; 1988). Good mechanical characteristics and high wear resistance are important requirements which must be fulfilled by a hard dental compound which is intended as a long-term replacement for lost hard natural dental substance.

But in addition to strengthening characteristics, the filling compounds also must fulfill other material parameters. An important parameter in this context is the polishability. High gloss polishability is of significant importance for filling materials and crown and bridge materials for at least two reasons:

A high-gloss and completely homogenous surface must be required of the filling material for aesthetic reasons, so that the filling cannot be distinguished from the surrounding, absolutely smooth, natural tooth enamel. This high-gloss filling surface also must retain its characteristic for a long period.

A highly smooth filling surface is also important so that plaque or discoloring media cannot attach themselves.

However, it has now been shown that the previously described finely ground quartz or glass fillers have good strengthening characteristics, but do not fulfill requirements in regard to their polishability. It has therefore been attempted to grind these fillers even finer in order to obtain more homogenous surfaces. However, physical grinding methods are limited, so that average grain sizes below 1 μm are hard to achieve.

When highly dispersed silica (average particle size 10 to 400 nm) was used as a filler in dental masses (German Patent 24 03 211) it was surprisingly shown that these fillers were able to achieve a significant improvement in polishability. Disadvantages of the highly dispersed silica result from its great thickening effect, so that today, as a rule, filling amounts above 52 wt % cannot be obtained, unless insufficient processing technology characteristics are tolerated.

The materials filled with highly dispersed silicic acid also showed clearly lower stabilities and hardness than those filled with quartz or finely ground glass.

SUMMARY OF THE INVENTION

It is an object of this invention to provide new photo-, heat- or self hardening dental materials containing a polymerizable organic bonding agent and a finely divided filler as essential ingredients, which on the one hand may be polished to high gloss and thus fulfill the aesthetic requirements of a dental material, but which on the other hand have better physical characteristics than the dental materials representing the present state of technology.

In attaining the above and other objects, one feature of the invention resides in new, pasty dental materials, which harden to a high-gloss polishable mass in the presence of an initiator, comprising a polymerizable bonding agent and a finely divided filler, which contains as a filler an organopolysiloxane which consists of units of the formula

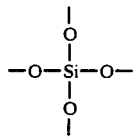

(I)

and units of the formula

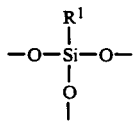

(II)

wherein $R^1$ stands for a linear or optionally branched alkyl group with 1 to 6 carbon atoms bonded with an acrylate or methacrylate residue or for a single olefinic unsaturated, preferably end-positioned unsaturated linear, optionally branched hydrocarbon residue with 2 to 8 carbon atoms or for a cyclic, single olefinic unsaturated hydrocarbon residue with 5 to 8 carbon atoms or for a linear, optionally branched alkyl group with 1 to 8 carbon atoms, a cycloalkylene group with 5 to 8 carbon atoms, a phenyl group or an alkylaryl group and/or units of the formula

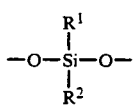

(III)

wherein $R^2$ represents a methyl, ethyl or phenyl group, and the free valences of the oxygen atoms bonded with the silicon atoms in the units (I), (II), (III) are as in the silica structures saturated by a silicon atom of a same or different unit whereby the ratio of silicon atoms of the units of Formula (I) to the sum of silicon atoms of units (II) and (III) is 3:1 to 100:1.

The units according to Formulas (I) to (III) may naturally be present in different forms in respect to each other, i.e. they may be present in the form of a statistical copolycondensate or in the form of a block-copolycondensate or in the form of a so-called mixed copolycondensate. According to the invention, the fillers of the new dental materials may in respect to the units according to Formulas (I) to (III) be present in any of the mentioned forms and their mixtures.

This means that in the case of a pure statistical copolycondensate which contains units of the Formula (I), (II), and/or (III) a pure statistical distribution of the components according to the molar ratios of the starting products is given.

In the case of a so-called block-copolycondensate, blocks of identical units according to Formula (I) and (II) and/or (III) form. Finally, a so-called mixed copolycondensate possesses structures of a statistical copolycondensate as well as of a block-copolycondensate.

The fillers according to the invention are used in the dental masses in an amount from 20 to 90 wt %, preferably 50 to 85 wt %. The unsaturated organic residue $R^1$ possibly also present at the units according to Formula (II) may in particular act to achieve a stronger bond between the polysiloxane filler and the polymer matrix which is later produced from the polymerizable organic bonding agent.

Organic residues $R^1$ in which a double bond is sterically readily accessible and in particular relatively easy to polymerize are therefore especially suitable. This applies in particular for the group

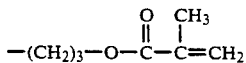

since it is known that it is especially easy to polymerize and since the polymer matrix to which the filler is to be added is as a rule a methacrylate system, as well as for linear hydrocarbon residues with end-positioned double bond, such as e.g. the vinylbutenyl- or octenyl residue. However, cyclic hydrocarbon residues with polymerizable double bonds are also suitable. But in many cases $R^1$ may be one of the organic residues without double bonds also mentioned under Formula (II) in claim 1.

DETAILED DESCRIPTION OF THE INVENTION

A particularly advantageous filler composition which is characterized by being readily obtainable and easily prepared especially by technical availability of the starting materials uses an organopolysiloxane as filler which consists only of the units of Formula (I) and the specific units of Formula (II)

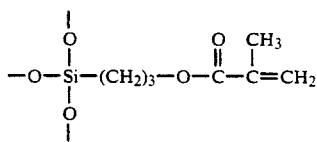

whereby the molar ratio of the units of Formula (I) to the units of Formula (II) is 3:1 to 100:1. Such a filler is characterized by the fact that it principally no longer requires silanization before being added to the methacrylate matrix, i.e. it no longer requires treatment with a methacrylsilane, since these methacryl groups are already present in the filler in a homogeneously distributed form.

But this does not exclude that in individual cases, in view of a further water-repellant finishing with further strengthening of the bonding between the organopolysiloxane filler and organic polymer matrix, an additional silanization of the filler is performed.

During the realization of the invention it was surprisingly discovered that very good mechanical characteristics and polishability of the dental material may also be achieved if the organopolysiloxane filler used contains no unsaturated, but only saturated residues $R^1$.

This applies for fillers which contain units according to Formula (I), (II) and (III) as well as for fillers which contain only units according to Formula (I) and (II). Such organopolysiloxane fillers without functional double bonds should, prior to their addition to the organic polymer matrix, be treated with a suitable organosilane compound, preferably 3-methacryloyloxy propyltrimethoxy- or 3-methacryloyloxy propyltriethoxysilane.

This applies analogously also for a filler composition according to the invention which is advantageous for reasons of especially ready availability of the starting materials and in which the polysiloxane is made up of units of Formula (I) and the specific units of Formula (III)

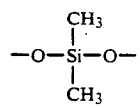

whereby the molar ratio of the units according to Formula (I) to the units of Formula (III) is 3:1 to 100:1.

The monomeric elements of the fillers according to the invention are principally known compounds, e.g. $Si(OC_2H_5)_4$ as monomeric element for a unit of Formula (I), a compound

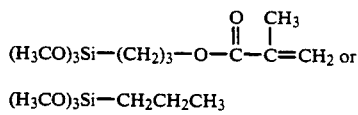

as monomeric elements for units of Formula (II) and a compound $(H_3C)_2Si(OC_2H_5)_2$ as monomeric element for units of Formula (III).

The compositions of the dental filling materials that may be produced from them may be described e.g. by formulas for a particular polymer unit such as

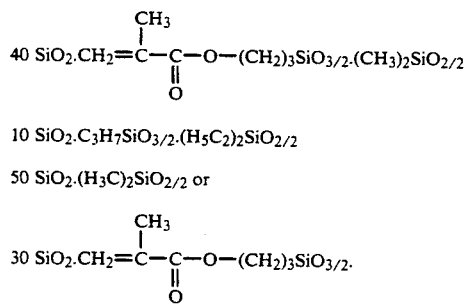

A typical acidic catalyst is e.g. hydrochloric acid or acetic acid, while amines are in addition to ammonia the typical basic catalysts.

In view of the physical characteristics the fillers of the composition according to the invention are particularly well suited for use in the dental materials according to the invention if they have a specific surface of about up to 200 m²/g, preferably about up to 100 m²/g, and a particle size from 0.01 μm to 100 μm, preferably 0.1 μm to 30 μm.

The fillers contained in the dental material according to the invention may be obtained according to various methods. One of these methods achieves this by dissolving an alkoxysilane of the general formula

whereby $R^3$ is a linear or branched alkyl group with 1 to 5 carbon atoms, and an alkoxysilane of the general formula

in which $R^1$ has the same meaning as in Formula (II), and/or an alkoxysilane of the general formula

in which $R^2$ has the same meaning as in Formula (III) in a mostly water-miscible solvent which, however, dissolves the silanes according to Formula (IV), (V) and (VI), and by adding to the solution while stirring an amount of water which is at least sufficient for the complete hydrolysis and condensation, then by precondensing the reaction mixture during continued stirring at a certain temperature ranging from room temperature to 200° C., by stirring the forming solid matter, optionally after addition of additional solvent or water, for 1 to 6 more hours at 60° C. to 200° C., at normal pressure or under a pressure which corresponds to the sum of partial pressures at the respective temperature, then post-treating the formed organopolysiloxane, optionally after a change of the medium and/or pH value, for another 4 hours to 5 days at 60° C. to 250° C. in the liquid phase, then separating according to standard methods from the liquid phase, optional washing, drying at room temperature up to 200° C., optionally in a controlled atmosphere or in vacuum, optional subsequent tempering for 1 to 100 hours at temperatures from 150° C. to 250° C. in a controlled atmosphere or in vacuum, optional grinding and/or classification, whereby the organopolysiloxane which has been separated from the liquid phase and optionally washed is prior to or after one of the phases of drying, tempering, grinding, classification treated in water, a water/alcohol mixture or in pure alcohol, in the presence of an acidic or basic catalyst, preferably in presence of ammonia, for a period of 1 hour to 5 days at temperatures from 60° C. to 250° C. under a pressure which corresponds to the sum of partial pressures at the respective temperature.

The advantageous application oriented technical characteristics of the new fillers are also based on the acidic or basic thermal treatment prior to or after the drying or in another of the optionally used treatment phases, since this results in particular in a strengthening of the polymer structure.

As a principle the corresponding halide or phenoxy compounds may be used in place of the alkoxy compounds as starting materials for the process. However, their use offers no advantages, but may e.g. in the case of chlorides result in problems because of the hydrochloric acid released during hydrolysis.

The hydrolysis of the monomers must be performed with an essentially water-miscible solvent which however dissolves the starting materials. Alcohols which correspond to the alkoxy groups at the monomeric starting materials are preferred.

Particularly suitable are methanol, ethanol, n- and isopropanol, n- and isobutanol and n-pentanol. Mixtures of such alcohols may also be used as solvents during the hydrolysis.

It is naturally also possible to use other polar solvents which are essentially water-miscible, but this is not very logical for reasons of process technology because of the solvent mixtures produced with the hydrolytically separated alcohol.

The hydrolysis is preferably performed with an excess of water above the stoichiometrically required amount. The amount of water required for hydrolysis depends on the hydrolysis speed of the respective monomer in such a manner that with an increasing amount of water the hydrolysis speeds up. However an upper limit may be given through segregation and forming of a two-phase system. As a rule hydrolysis is preferred in a homogenous solution.

Because of the mentioned aspects, in practice that maximum amount of water (in weight) is used as is used overall at silane monomers.

The polycondensation may be performed at different temperatures. Since the polycondensation is fastest at higher temperatures it is preferably performed at reflux temperature or slightly below. In principle the hydrolysis and polycondensation may still be performed at still higher temperature than reflux temperature, i.e. under pressure.

During polycondensation the reaction mixture may congeal into a solid mass. For this reason it is useful to add a corresponding amount of solvent or water for dilution.

As a rule, the solvent here will be the same as the one already used during hydrolysis of the silanes, i.e. preferably a lower alcohol with 1 to 5 carbon atoms.

As an alternative to the dilution with a solvent, it is naturally also possible to dilute with water. Whatever is used in the individual case depends on which physical characteristics are desired in the copolycondensate to be produced.

This may also be influenced by the duration and temperature of after-treatment in the liquid phase or in dry form. An after-reaction at higher temperature always results in a strengthening of the polymer structure and in an improvement of the mechanical properties.

The separation of the formed solid matter may be performed according to standard methods, such as filtration, decantation, centrifugation or distilling off of the liquid phase. The washing of the formed solid matter is preferably performed with the solvent used during the separation or with water.

The dried or tempered product may be ground in the usual devices and may be classified into various grain size fractions. Depending on the circumstances, one or the other of the finishing measures washing, drying, tempering, grinding and classification may be foregone, or they may be performed in a different sequence.

A classification may e.g. also be performed at the wet product which may have been optionally dried or tempered before.

The duration of the hydrolysis depends on the hydrolysis suitability of the starting materials and on the temperature. The hydrolysis temperature depends in particular on the alkoxy groups located at the silicon whereby the methoxy group hydrolyzes fastest and the process is slowed down with increasing chain length or increasing branching.

Hydrolysis and polycondensation may be accelerated by addition of organic or inorganic bases, e.g. ammonia or amines, or organic or inorganic acids, e.g. hydrochloric acid, or by the standard condensation catalysts, e.g. dibutyl tindiacetate.

In order to compensate for different hydrolysis and polycondensation characteristics of the monomeric components of a statistical copolycondensate, the monomeric components according to Formula (IV), (V) and/or (VI) may be precondensed according to one production version. For this purpose the monomeric components—with or without the use of a solvent dissolving the starting materials, preferably linear or branched alcohols with 1 to 5 carbon atoms corresponding to the alkoxy groups—are precondensed in the presence of an amount of water insufficient for complete hydrolysis, preferably 1 to 100 mol % of the amount required for it, for a period of 5 min to 5 days at room temperature to 200° C.

In order to promote this precondensation effect an acidic or basic condensation catalyst may be added to the process. Preferred catalysts are e.g. hydrochloric acid, acetic acid, ammonia, soda lye or caustic potash solution which are used in gas form or dissolved in water or in an organic solvent.

After the precondensation has been performed the complete hydrolysis and polycondensation, after optional addition of further water and optional addition of further solvent, is performed as described.

According to a different method so-called block copolycondensates are obtained in which blocks of identical units according to formula (I) and (II) and/or (III) have been formed. In this method the monomeric components according to Formula (IV), (V) and/or (VI), respectively independent from each other, are precondensed with or without the use of a solvent dissolving the starting materials, preferably a linear or branched alcohol with 1 to 5 carbon atoms corresponding to the alkoxy groups, in the presence of an amount of water insufficient for complete hydrolysis, preferably 1 to 100 mol % of the amount needed for this, for a period of 5 min to 5 days at room temperature to 200° C., the obtained condensates are combined and then, after optional addition of additional water and/or optional addition of additional solvent, the complete hydrolysis and polycondensation is performed as described.

Naturally, it is also possible to use one of the above mentioned condensation catalysts in the production version according to the invention.

According to another method so-called mixed copolycondensates are obtained in which a partial formation of blocks of identical units according to Formula (I) and (II) and/or (III) is present, but in which at least one monomeric component is always not precondensed and at least one monomeric component is precondensed.

This method is characterized by precondensing from the monomeric components according to Formula (IV), (V) and/or (VI) at least one monomer, but no more than 2 monomers, independent from each other, with or without use of a solvent dissolving the starting materials, preferably a linear or branched alcohol with 1 to 5 carbon atoms corresponding to the alkoxy groups, in the presence of an amount of water insufficient for complete hydrolysis, preferably in the presence of 1 to 100 mol % of the amount required for this, for a period from 5 min to 5 days at room temperature to 200° C., by combining the obtained precondensate or the obtained precondensates and at least one unprecondensed component with each other, and by then performing—after optional addition of additional water and/or optional addition of additional solvent—the complete hydrolysis and polycondensation as described.

The use of an acidic, basic and/or metal-containing condensation catalyst for precondensation is also feasible in this production version and the further treatment of the formed polycondensate takes place as in the other described production processes.

During the performance of the precondensation the amount of water used depends on the oligomerization degree to be obtained, i.e. which block size is to be attained. If more water and a longer precondensation time are used for precondensation this results naturally as a rule in larger units than if less water and a shorter reaction time are used. The duration of the precondensation depends, as already described above, in general naturally also on the hydrolysis readiness of the monomeric components and on the temperature.

The fillers for the new dental materials are characterized in particular by the quantitative hydrolysis and condensation yield and elementary analyses. In purely optical respects there is no difference between the copolycondensate obtained according to the various production processes. Depending on the treatment the fillers according to the invention have surfaces of about 0 to 200 $m^2/g$. The desired particle size diameters of 0.01 $\mu m$ to 100 $\mu m$ may be set without difficulty by using standard grinding techniques.

Another object of the invention is the use of the dental material for the production of dental fillings, inlays, dental sealants, coatings to protect tooth surfaces, crowns, veneers, bridges, dentures, artificial teeth, bonders for the attachment of inlays, crowns and bridges and for the building up of tooth stumps.

The invention is further explained by the following illustrative examples.

1. Preparation of Filling Materials to be Used in Accordance with the Invention

EXAMPLE 1

1,465.2 g (7.03 mol) $Si(OC_2H_5)_4$ and 34.8 g (0.234 mol) $(CH_3)_2Si(OC_2H_5)_2$ were dissolved in 750 ml ethanol. The solution was heated to reflux temperature and then 525 ml of 10% aqueous ammonia solution was added. It was first stirred for 30 min with reflux, then the formed solid matter was diluted with 750 ml of water. After another 2 hours of stirring the suspension was cooled with reflux to room temperature and the formed white solid matter was filtered off the liquid phase and washed with a total of 500 ml of water. 700 ml of 2% $NH_3$ solution were added to the solid matter and it was then transferred into an autoclave. After treatment of the autoclave content for 24 hours at 150° C. the solid matter was dried for 24 hours at 120° C. in the dryer in $N_2$ atmosphere and then ground for 24 hours in a ball mill.

The yield was 437.2 g (99.4% of theoretical yield) of a dental filling material, consisting of polymer units of the formula $(CH_3)_2SiO_{2/2}.30\ SiO_2$.

| Analyses: | Specific surface: 22 $m^2/g$ | | |
|---|---|---|---|
| | % C | % H | % Si |
| Theory: | 1.28 | 0.32 | 46.4 |
| Actual: | 1.12 | 0.40 | 45.6 |

EXAMPLE 2

1,456.5 g (6.99 mol) of $Si(OC_2H_5)_4$ and 43.5 (0.175 mol) of methacryloyloxy propyltrimethoxysilane were combined in 750 ml of ethanol. The solution was heated in a 6 l Woulff bottle (3 neck flask) with KPG agitator and reflux condenser to reflux temperature while stirring and 500 ml of 5% $NH_3$ solution was added to it at boiling point. After ca. 30 min of stirring with reflux the formed white solid matter was diluted with 750 ml of water. Stirring was continued for another 5 h with reflux; then the suspension was cooled to room temperature and the solid matter was filtered off from the liquid phase. 500 ml of 5% ammonia solution was added to the solid matter and it was then transferred to an autoclave.

After stirring the autoclave contents for 48 h at 130° C. the ammonia was washed off the solid matter and it was then dried for 24 h at 100° C. in N₂ atmosphere and then ground for 12 h in a ball mill. The yield was 450 g (99.6% of theoretical yield) of a dental filling material consisting of units of the formula

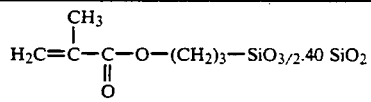

| Specific surface: 23 m²/g | | | |
|---|---|---|---|
| Analyses: | % C | % H | % Si |
| Theory: | 3.26 | 0.43 | 44.6 |
| Actual: | 3.12 | 0.34 | 44.0 |

EXAMPLE 3

1,431.8 g (6.87 mol) of Si(OC₂H₅)₄, 42.7 g (0.172 mol) of methacryloyloxy propyltrimethoxysilane and 25.5 g of (CH₃)₂Si(OC₂H₅)₂ were combined in 750 ml of methanol. The solution was heated to reflux temperature and then 400 ml of 5% ammonia solution were added to it. After following the procedures analogous to Example 2, 450 g (98.6% of theoretic yield) of a dental filling material consisting of units of the formula

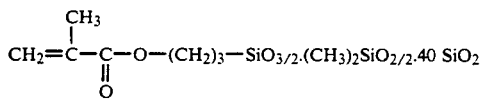

were obtained.

| Specific surface: 32 m²/g | | | |
|---|---|---|---|
| Analyses: | % C | % H | % Si |
| Theory: | 4.07 | 0.64 | 44.4 |
| Actual: | 3.82 | 0.59 | 43.4 |

EXAMPLE 4

722.9 g (3.47 mol) of Si(OC₂H₅)₄, 14.3 g (0.0867 mol) of n—C₃H₇—Si(OCH₃)₃ and 12.9 g (0.0867 mol) of (CH₃)₂Si(OC₂H₅)₂ were dissolved in 375 ml of ethanol. The solution was heated to reflux temperature and 200 ml of 1n-HCl solution were added to it. After 1 h the solid matter formed and was diluted with 400 ml of methanol, and was then stirred for another 30 min with reflux. The solid matter was subsequently filtered off, 500 ml of 10% ammonia solution were added to it, and it was stirred for another 15 h in an autoclave at 150° C. After further processing according to Example 2 the yield was 220.0 g (98.6% of theoretic yield) of a dental filling material consisting of units of the formula

| n-C₃H₇SiO₃/₂.(CH₃)₂SiO₂/₂.40 SiO₂ | | | |
|---|---|---|---|
| Specific surface: 56 m²/g | | | |
| Analyses: | % C | % H | % Si |
| Theory: | 2.3 | 0.51 | 45.9 |
| Actual: | 2.1 | 0.40 | 44.8 |

EXAMPLE 5

727.8 g (3.49 mol) of Si(OC₂H₅)₄ and 22.2 g (0.1165 mol) of CH₂=CH-Si(OC₂H₅)₃ were combined with each other. 3 ml of 0.1 n acetic acid solution was added to the mixture and it was stirred for 3 h at 80° C.

After this precondensation 400 ml of ethanol and 200 ml of water were added to the mixture and it continued to be stirred. After 2 h of reflux the solid matter formed and was filtered. After washing with a total of 1 liter of water it further processed analogously to Example 4. The yield was 216.0 g (98.5 % of theoretic yield) of a dental filling material consisting of units of the formula

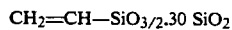

| Specific surface: 22 m²/g | | | |
|---|---|---|---|
| Analyses: | % C | % H | % Si |
| Theory: | 1.28 | 0.16 | 46.3 |
| Actual: | 1.17 | 0.20 | 45.8 |

EXAMPLE 6

To 727.8 g (3.49 mol) of Si(OC₂H₅)₄ 2 ml of 1% aqueous ammonia solution were added and it was stirred for 2 h at 100° C. At the same time 5 ml of ethanol and 0.5 ml of 2% aqueous ammonia solution were added to 19.0 g (0.07 mol) of (C₆H₅)₂Si(OC₂H₅)₂ and it was stirred for 10 h at 100 C. The two precondensates were then combined and 500 ml of ethanol as well as 150 ml of 2% aqueous NH₃ solution were added, and it was stirred for an additional 3 h with reflux. The formed solid matter was filtered off and was after washing with 500 ml of ethanol further processed analogous to Example 4.

After a concluding 24 h tempering at 150° C. in N₂ atmosphere 220.0 g (98.1% of theoretical yield) of a dental filling material consisting of units of the formula

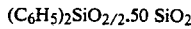

were obtained.

| Specific surface: 31 m²/g | | | |
|---|---|---|---|
| Analyses: | % C | % H | % Si |
| Theory: | 4.50 | 0.31 | 44.7 |
| Actual: | 4.40 | 0.26 | 43.9 |

EXAMPLE 7

To 17.3 g (0.087 mol) of (C₆H₅)Si(OCH₃)₃ 0.2 ml of 2% methanolic NH₃ solution were added and it was first stirred for 5 h at 60° C. Then the precondensate was combined with 727.8 g (3.49 mol) of Si(OC₂H₅)₄. After further processing analogously to Example 7 216.3 g (98.2% of theoretic yield) of a dental filling material consisting of units of the formula

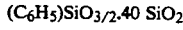

were obtained

| Specific surface: 48 m²/g | | | |
|---|---|---|---|
| Analyses: | % C | % H | % Si |
| Theory: | 2.85 | 0.20 | 45.5 |
| Actual: | 2.95 | 0.31 | 45.8 |

II. Preparation of the Dental Materials According to the Invention

To produce the dental masses according to the invention the filling materials of Examples 1 to 5 were ground with a ball mill to an average grain size of between ca. 3 to 7 μm. The fillers were then according to standard procedures silanized with 3-methacryloyloxy propyltrimethoxysilane.

The fillers were in amounts from ca. 70 to 73% (m/m) added to a monomer matrix as it is usually used for dental plastics. Then initiators were added and the masses were kneaded into homogeneous pastes.

A number of physical characteristics was determined with the help of hardened test bodies prepared from the various pastes and were compared to those of commercially available products and laboratory test products (Table 1).

Testing and Evaluation of Polishability

Test bodies with a diameter of 15 mm and a thickness of 3 mm were produced from all materials. The surfaces of all test bodies were first evenly sanded with fine sanding paper (600 grit). Then they were polished on a cotton cloth under water with superfine aluminum oxide (average particle size 0.04 μm).

The polishability was evaluated visually and graded with the help of a point scale ranging from 1 to 5 with 1=dull and 5=high gloss. Examples of dental masses according to the invention

1. Heat-Hardened Dental Masses According to the Invention.

The production of the test bodies of the heat-hardened dental masses according to the invention took place in such a way that the masses were pressed into the respective test body molds and were then hardened at 90° C. for 30 min in a water bath at 6 atmospheres above atmospheric pressure.

The following examples use these abbreviations:

| Example 9 (numbers in weight parts): |
| --- |
| 73.0 filler according to Example 1 |
| 18.2 bis-GMA |
| 8.5 TEDMA |
| 0.3 dibenzoylperoxide |
| Example 10 (numbers in weight parts): |
| 70.0 filler according to Example 2 |
| 20.3 bis-GMA |
| 9.4 TEDMA |
| 0.3 dibenzoylperoxide |
| Example 11 (numbers in weight parts): |
| 70.0 filler according to Example 3 |
| 20.3 bis-GMA |
| 9.4 TEDMA |
| 0.3 dibenzoylperoxide |
| Example 12 (numbers in weight parts): |
| 71.0 filler according to Example 4 |
| 19.6 bis-GMA |
| 9.1 TEDMA |
| 0.3 dibenzoylperoxide |
| Example 13 (numbers in weight parts): |
| 73.0 filler according to Example 5 |
| 18.2 bis-GMA |
| 8.5 TEDMA |
| 0.3 dibenzoylperoxide | bis-GMA: 2,2-bis-[p-(methacryloyloxy-β-hydroxypropoxy)-phenyl]-propane
TEDMA: tirethyleneglycoldimethacrylate

2. Optically Hardening Dental Masses According to the Invention

The optically hardening dental mass according to the invention consists of a white paste which is hardened through irradiation with a dental halogen lamp (Translux, Kulzer Company). Irradiation time 100 sec.

| Example 14 (Number in weight parts): |
| --- |
| 70.0 filler according to Example 2 |
| 19.0 bis-GMA |
| 8.7 TEDMA |
| 0.2 camphorquinone |
| 0.1 N,N-dimethyl-p-toluidine |

Commercially available products with which the dental masses according to the invention are compared in Table 1:

Conventional composites (Estilux, Kulzer Company):

The filler is a silanized lithium aluminum glass with an average grain size of ca. 4 μm. The filler content is ca. 75% (m/m). Hybrid composites (Degufill H, Degussa):

The filler is silanized barium aluminumsilicate glass with an average grain size of ca. 2 μm, which is however 100% finer than 5 μm, as well as silanized, highly dispersed $SiO_2$. The filling degree of glass is ca. 70% (m/m), that of highly dispersed $SiO_2$ ca. 11% (m/m). This results in a total inorganic filler content of ca. 8% (m/m).

Microfiller composites (Durafill, Kulzer & Co., GmbH):

The filler is silanized, highly dispersed $SiO_2$ with an average grain size between 0.01 to 0.04 μm. The filling degree is ca. 50% (m/m).

The hardening of all masses was performed with the Translux lamp (Kulzer Company) and an irradiation time of 40 sec. Heat-hardening laboratory test products=VP (Numbers in weight parts):

| VP1: | 17 bis-GMA |
| --- | --- |
| | 7.7 TEDMA |
| | 75 bariumaluminumsilicate glass, silanized (average grain size ca. 4 μm) |
| | 0.3 dibenzoylperoxide |
| VP2: | 35 bis-GMA |
| | 14.7 TEDMA |
| | 50 highly dispersed, $SiO_2$, silanized (average grain size 0.01–0.04 μm) |
| | 0.3 dibenzoylperoxide |

The hardening of these pastes took place analogously to the heat-hardening masses according to the invention.

TABLE 1

Characteristics of the Dental Masses According to the Invention in Comparison with Commercially Available Products and with Conventional and Microfilled Heat-Hardening Dental Masses

| Beispiel[1] | 9 | 10 | 11 | 12 | 13 | 14 | Estilux | Durafill | Degufill H | VP1 | VP2 |
| --- | --- | --- | --- | --- | --- | --- | --- | --- | --- | --- | --- |
| Biegefestigkeit[2] | 125 | 130 | 80 | 118 | 120 | 90 | 100 | 62 | 110 | 140 | 65 |

TABLE 1-continued

Characteristics of the Dental Masses According to the Invention in Comparison with Commercially Available Products and with Conventional and Microfilled Heat-Hardening Dental Masses

| Beispiel[1] | 9 | 10 | 11 | 12 | 13 | 14 | Estilux | Durafill | Degufill H | VP1 | VP2 |
|---|---|---|---|---|---|---|---|---|---|---|---|
| [N/mm$^2$] DIN 13 Biegemodul[3] [N/mm$^2$] DIN | 8500 | 9000 | 10700 | 7500 | 8000 | 7600 | 9700 | 322 | 8000 | 11000 | 3900 |
| Druckfestigkeit[4] [N/mm$^2$] | 435 | 400 | 450 | 460 | 470 | 280 | 300 | 350 | 320 | 350 | 410 |
| Vickers Harte[5] HV 5 | 1100 | 860 | 750 | 780 | 820 | 830 | 660 | 290 | 680 | 660 | 330 |
| Polierbarkeit[6] | 5 | 5 | 5 | 5 | 5 | 5 | 1 | 4 | 3 | 1 | 4 |

Key:
[1] example
[2] flectional strength
[3] flexion module
[4] pressure resistance
[5] pyramid hardness
[6] polishability

We claim:

1. A pasty dental material able to harden to a high-glass polishable mass in the presence of an initiator, comprising a polymerizable bonding agent which is a monofunctional or multifunctional ester of methacrylate acid or mixtures thereof, and a fine particle filler, wherein the filler is an organopolysiloxane which consists of units of formula I

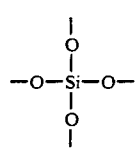
(I)

in combination with at least one member selected from the group consisting of: units of formula II and units of formula III, wherein the units of the formula II are as follows:

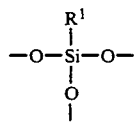
(II)

wherein R$^1$ stands for a linear or branched alkyl group with 1 to 6 carbon atoms bonded with an acrylate or methacrylate residue, or for a single olefinic unsaturated, linear, optionally branched hydrocarbon residue with 2 to 8 carbon atoms, or for a cyclic, single olefinic unsaturated hydrocarbon residue with 5 to 8 carbon atoms, or for a linear, optionally branched alkyl group with 1 to 8 carbon atoms, a cycloalkylene group with 5 to 8 carbon atoms, a phenyl group or an alkyaryl group, and the units of the formula III are as follows:

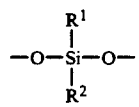
(III)

wherein R$^2$ represents a methyl, ethyl or phenyl group, and the free valences of the oxygen atoms bonded with the silicon atoms in the units of formulas (I), (II), (III) are as in polymeric silicic acid SiO$_{4/2}$ saturated by a silicon atom of a same or different unit whereby the ratio of silicon atoms of the units of Formula (I) to the sum of silicon atoms of units of formulas (II) and (III) is 3:1 to 100:1, said organopolysiloxane having been heated in water or in water—alcohol mixture or in pure alcohol, in the presence of an acidic or basic catalyst at a temperature of 60° C. to 250° C. for 1 hour to 5 days under a pressure which corresponds to the sum of partial pressures at the respective temperature.

2. The dental material according to claim 1, wherein the filler is present as a random copolycondensate, block-copolycondensate or as a mixture thereof.

3. The dental material according to claim 1 wherein R$^1$ stands for the group

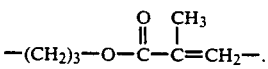

4. The dental material according to claim 1 wherein an organopolysiloxane is used as filler which consists of units of Formula (I) and units of Formula (II) with the formula

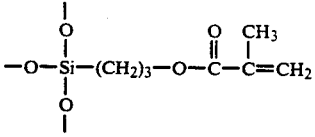

whereby the molar ratio of the Formula (I) units to the Formula (II) units is 3:1 to 100:1.

5. The dental material according to claim 1 wherein an organopolysiloxane is used as filler which consists of Formula (I) units and Formula (III) units with the formula

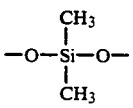

whereby the molar ratio of the Formula (I) units to the Formula (III) is 3:1 to 100:1.

6. The dental material according to claim 1 wherein the filler has a specific surface of up to 200 m²/g, and a particle size of 0.01 μm to 100 μm.

7. The dental material according to claim 6 wherein the surface is up to 100 m²/g.

8. The dental material according to claim 6 wherein the particle size is 0.1 μm to 30 μm.

9. The dental material according to claim 1 wherein the filler is in the form of a random copolycondensate prepared by a process comprising dissolving an alkoxysilane of the formula $$Si(OR^3)_4 \qquad (IV)$$

wherein $R^3$ is a linear or branched alkyl group with 1 to 5 carbon atoms, and an alkoxysilane of the formula $$R^1-Si(OR^3)_3 \qquad (V)$$

in which $R^1$ has the same meaning as in Formula (II), and/or an alkoxysilane of the formula $$(R^2)_2Si(OR^3)_2 \qquad (VI)$$

in a water-miscible solvent which, however, dissolves the silanes according to Formula (IV), (V) and (VI), and by adding to the solution while stirring an amount of water which is at least sufficient for the complete hydrolysis and condensation, then by precondensing the reaction mixture during continued stirring at a certain temperature ranging from room temperature to 200° C., by stirring the forming solid matter, optionally after addition of another solvent or water, for 1 to 6 more hours at 60° C. to 200° C., at normal pressure or under a pressure which corresponds to the sum of partial pressures at the respective temperature, then post-treating the formed organopolysiloxane, optionally after a change of the medium and/or pH value, for another 1 hour to 5 days at 60° C. to 250° C. in the liquid phase, then separating according to standard methods from the liquid phase, optional washing, drying at room temperature up to 200° C., optionally in a controlled atmosphere or in vacuum, optional subsequent tempering for 1 to 100 hours at temperatures from 150° C. to 250° C. in a controlled atmosphere or in vacuum, optional grinding and/or classification, whereby the organopolysiloxane which has been separated from the liquid phase and optionally washed is prior to or after one of the phases of drying, tempering, grinding, classification treated in water, a water/alcohol mixture or in pure alcohol, in the presence of an acidic or basic catalyst, preferably in presence of ammonia, for a period of 1 hour to 5 days at temperatures from 60° C. to 250° C. under a pressure which corresponds to the sum of partial pressures at the respective temperature.

10. A method of using the dental material according to claim 1 comprising shaping the composition into a dental filling, inlay, veneer, seal, crown, bridge, denture or artificial tooth.

11. The method of using the dental material according to claim 1 as an adhesive comprising applying said material to an inlay, crown or bridge and adhering the inlay, crown or bridge to a structure underlying said inlay, crown or bridge.

12. The pasty dental material according to claim 1 wherein $R^1$ is a single olefinic end positioned unsaturated linear hydrocarbon residue of 2 to 8 carbon atoms.

* * * * *